(12) United States Patent
Momotani et al.

(10) Patent No.: US 7,731,937 B2
(45) Date of Patent: Jun. 8, 2010

(54) DIAGNOSTIC METHOD FOR PARATUBERCULOSIS

(75) Inventors: Eiichi Momotani, Tsukuba (JP); Yasuyuki Mori, Tsukuba (JP); Hirokazu Hikono, Tsukuba (JP); Joram Josephat Buza, Tsukuba (JP)

(73) Assignee: Incorporated Administrative Agency National Agriculture and Bio-Oriented Research Organization, Tsukuba-shi, Ibaraki (JP)

( * ) Notice: Subject to any disclaimer, the term of this patent is extended or adjusted under 35 U.S.C. 154(b) by 0 days.

(21) Appl. No.: 10/572,514

(22) PCT Filed: Sep. 17, 2003

(86) PCT No.: PCT/JP03/11845

§ 371 (c)(1),
(2), (4) Date: Apr. 26, 2007

(87) PCT Pub. No.: WO2005/029079

PCT Pub. Date: Mar. 31, 2005

(65) Prior Publication Data

US 2008/0038758 A1   Feb. 14, 2008

(51) Int. Cl.
*A61K 48/00* (2006.01)
*A61K 39/04* (2006.01)
*C12N 5/00* (2006.01)

(52) U.S. Cl. ............... 424/9.1; 424/9.2; 424/130.1; 424/158.1; 424/184.1; 424/234.1; 424/248.1; 424/85.2; 424/85.4; 424/85.5; 435/386

(58) Field of Classification Search .......... 424/9.1, 424/9.2, 130.1, 158.1, 184.1, 234.1, 248.1, 424/85.2, 85.4, 85.5; 435/386
See application file for complete search history.

(56) References Cited

U.S. PATENT DOCUMENTS 5,679,347 A * 10/1997 Porcelli et al. ........... 424/184.1

OTHER PUBLICATIONS

Koets, A.P., et al. Heat-shock protein-specific T-cell response in various stages of bovine paratuberculosis. Veterinary Immunology and Immunopathology. vol. 70, No. 1-2, pp. 105-115, 1999.*

Cole, S.T. Comparative mycobacterial genomics as a tool for drug target and antigen discovery. Eur. Respir. J., vol. 20, Suppl. 36, pp. 78s-86s, 2002.*

Lind, A. Mycobacterial species: immunological classification, in, The Mycobacteria, ed. G.P. Kubica and L.G. Wayne, Marcel Dekker, Inc., New York, pp. 67-82, 1984.*

Merkel, R.S. Paratuberculosis, in, The Mycobacteria, ed. G.P. Kubica and L.G. Wayne, Marcel Dekker, Inc., New York, pp. 1237-1249, 1984.*

Coussens et al."Gene expression profiling of peripheral blood monouclear cells from cattle infected with *Mycobacterium paratuberculosis*", Infection and Immunity, vol. 70, No. 10 Oct. 2002.

Weiss et al., "Differential responses of bovine macrophages to *Mycobacterium avium* subsp. *Paratuberculosis*", Infection and Immunity, vol. 70, No. 10 (2002) pp. 5556 to 5561.

Olsen et al. "Elevated antibody responses in patients with Crohn's disease against a 14-kDa secreted protein purified from *Mycobacterium avium* subsp. *Paratuberculosis*", Scandinavian Journal of Immunology, vol, 53. No. 2 (2001). pp. 198 to 203.

* cited by examiner

*Primary Examiner*—Rodney P. Swartz
(74) *Attorney, Agent, or Firm*—Antonelli, Terry, Stout & Kraus, LLP.

(57) ABSTRACT

The present invention is intended to provide a diagnostic method for *paratuberculosis* by which an animal infected with *Mycobacterium avium* subsp. *Paratuberculosis* can be diagnosed at a high sensitivity in the sub-clinical infection stage before the specific antibody level begins to increase and a large number of specimens can be treated. The present invention provides: a diagnostic method for *paratuberculosis* characterized by collecting the blood of a subject animal, adding an anti-IL-10 antibody and a *Mycobacterium avium* subsp. *Paratuberculosis* antigen to the collected blood followed by culture, and then measuring the amount of produced IFNγ in the blood; a diagnostic method for *paratuberculosis* characterized in that the amount of produced IFNγ in blood is measured by the IFNγ ELISA method; and a diagnostic method for mycobacterial infection characterized by collecting the blood of a subject animal, adding an anti-IL-10 antibody and a mycobacterial antigen to the collected blood followed by culture, and then measuring the amount of produced IFNγ in the blood.

4 Claims, 7 Drawing Sheets

DIAGNOSTIC METHOD FOR PARATUBERCULOSIS

TECHNICAL FIELD

The present invention relates to diagnostic method for paratuberculosis (Johne's disease), and more specifically to improvement of the sensitivity, to application in an early stage of the infection before increase of the specific antibody and to use large scale field application.

BACKGROUND ART

Paratuberculosis is caused by Mycobacterium avium subsp. paratuberculosis that is one of acid-fast bacteria, and is a chronic granulomatous diarrheal infectious disease in ruminants such as cattle, goats, sheep, and buffalos. With regard to pandemic of bovine paratuberculosis in Japan, the increase of infected animals and the expansion of the outbreak areas have been seen since 1980. In particular, the outbreak numbers increased at a rate of 100 to 200 cattle/year from the 1990s, and exceeded 800 in 2000.

Figure 1:
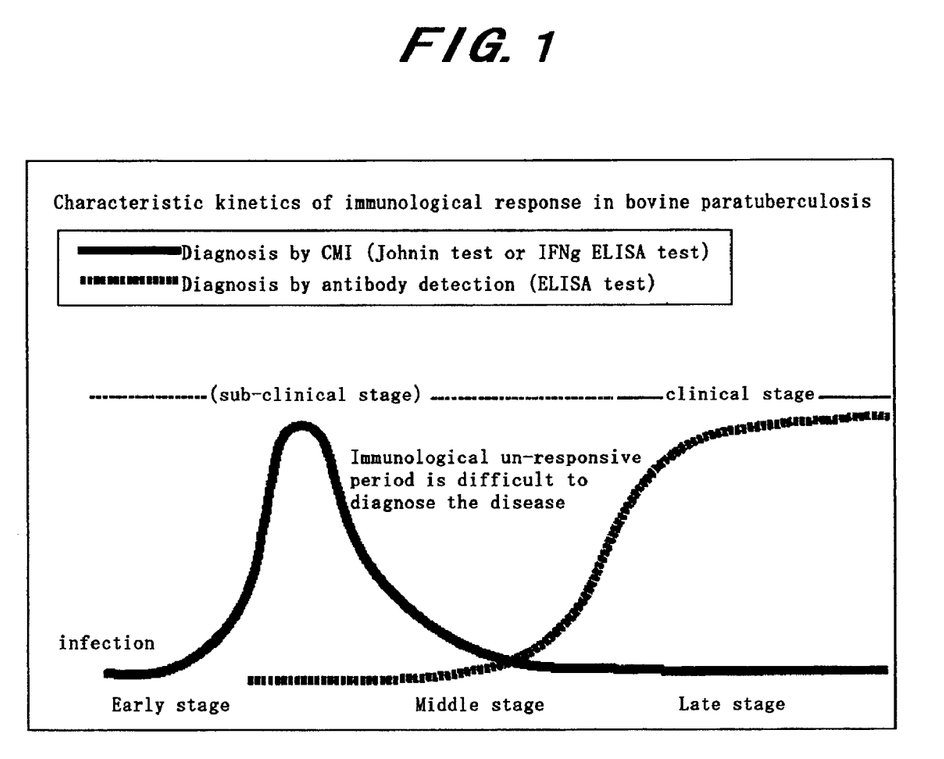
FIG. 1 shows the course of infection (from infection to onset of symptoms) of *paratuberculosis* and shift in immune response.

FIG. 1 shows the course of infection (from infection to onset of symptoms) of paratuberculosis and shift in immune response. Paratuberculosis is developed by oral infection of Mycobacterium avium subsp. paratuberculosis in the early period after birth. However, most of the routes of infection are still unclear, and differences in the course of the disease between individuals are larger than those in any other diseases.

The sub-clinical infection stage between infection and onset of symptoms, (clinical signs such as diarrhea are observed), is generally 2 to 5 years or more. In some individuals, the period is about ten years or more, or the symptoms are not found throughout their life. From this standpoint, paratuberculosis is considered as an "ultrachronic infection".

The ELISA method is a diagnostic method involving detecting a specific antibody against Mycobacterium avium subsp. paratuberculosis, and is prevalent all over the world because of its simplicity (see Momotani Eiichi "Up-to-date information on diagnosis of bovine Johne's disease", Journal of Clinical Veterinary Medicine, vol. 16 (9), 1998, 24-31, in Japanese). However, the method can be used in diagnosing cattle in advanced stage, or after increase of antibody level, but cannot diagnose sub-clinically infected animals before the specific antibody level increases. However, as a result of prevalence of this ELISA method as a standard for diagnosis of paratuberculosis, sub-clinically infected animals that cannot be diagnosed by the ELISA method relatively increases, although ELISA-positive cattle decreases. Therefore, the diagnosis becomes increasingly harder.

Meanwhile, as shown in FIG. 1, the cell-mediated immunity of an animal infected with Mycobacterium avium subsp. paratuberculosis is induced at the early stage of infection but is then gradually decreased. Examples of diagnostic methods of such cell-mediated immunity include a johnin reaction and an interferon γ (IFNγ) ELISA method.

The Johnin reaction (johnin intradermal reaction) is a diagnostic method of detecting the cell-mediated immunological response of a host against Mycobacterium avium subsp. paratuberculosis and is an intradermal reaction similar to the tuberculin reaction in tuberculosis. That is, the diagnosis is performed by: intradermally injecting a culture supernatant of Mycobacterium avium subsp. Paratuberculosis (Mycobacterium avium subsp. paratuberculosis PPD, Johnin PPD) to the root of the tail of a subject animal; and observing and measuring the redness and swelling at the injection site again. The method has been conventionally used, and also in Japan, this method is employed as a diagnostic method for paratuberculosis in the Domestic Animal Infectious Disease Control Law.

However, johnin reaction requires two visits to a farm for diagnosing and moreover, in the case of many subject animals to be tested, requires more labor and time, so that it is unfavorable for the test of a large number of specimens. Therefore, to detect a specific antibody, the ELISA method tends to be more widely performed in the world than johnin reaction.

On the other hand, the IFNγ ELISA method is a method of detecting the amount of produced IFNγ in vitro utilizing a cell-mediated immunological response against Mycobacterium avium subsp. paratuberculosis (see Billman-Jacobe H, Carrigan M, Cockram F, Corner L A, Gill I J, Hill J F, Jessep T, Milner A R, Wood P R, 1992. A comparison of the interferon gamma assay with the absorbed ELISA for the diagnosis of Johne's disease in cattle. Aust Vet J. 69:25-28). When the peripheral blood of a sub-clinically infected cattle that has been infected with Mycobacterium avium subsp. Paratuberculosis and a cattle that develops the disease are stimulated by a Mycobacterium avium subsp. paratuberculosis antigen, IFNγ that is one of cytokines is produced in large amounts by the sub-clinically infected cattle. Therefore, it was revealed that the amount of produced IFNγ is effective in diagnosis of a sub-clinically infected cattle, (see Stabel J R, 1996. Production of gamma-interferon by peripheral blood mononuclear cells: an important diagnostic tool for detection of subclinical paratuberculosis. J Vet Diagn Invest. 8:345-350) and the present method was introduced in the 1990s.

The IFNγ ELISA method enables more sensitive diagnosis of infection of paratuberculosis than johnin reaction also utilizing a cell-mediated immunological response, but the sensitivity is lowered as the cell-mediated immunity is gradually decreased, resulting in undetectable levels. Meanwhile, various factors (such as the stage of infection and proliferation level of Mycobacterium avium subsp. paratuberculosis in a lesion) may also decrease the sensitivity, so that the method still has problems as a diagnostic method.

Meanwhile, there has also been studied a diagnostic method using, as an index, a phenomenon in which a T-lymphocyte that recognizes a Mycobacterium avium subsp. Paratuberculosis antigen reacts and induces cell proliferation thereof when the lymphocyte is exposed to the antigen again (lymphocyte blastogenesis reaction, lymphocyte proliferation reaction) (see Kreeger J M, Snider T G 3rd., 1992. Measurement of lymphoblast proliferative capacity of stimulated blood mononuclear cells from cattle with chronic paratuberculosis. Am J Vet Res. 53:392-395). However, the method requires use of a radioactive isotope for proliferation of the lymphocyte, so it is not suitable for field diagnostic applications and therefore is not practical.

As described above, the infection period of Mycobacterium avium subsp. paratuberculosis includes a long sub-clinical stage of infection as described above, which further includes an immunological un-responsive period difficult to diagnose the disease when diagnosis cannot be achieved by either of cell-mediated immunity or detection of a specific antibody. Moreover, the period varies greatly from individual to individual and is long (3 to 5 years), so that it is impossible to find infected animals effectively by domestic epidemic prevention or by import quarantine, which makes it difficult to eradicate paratuberculosis.

An infected animal in the sub-clinical stage of infection has a certain lesion sustainably, and microorganisms are irregularly excreted in feces, so that the feces serve as contamination sources and cause spread of infection. In particular, from the aspect of epidemic prevention, they cause big problems in the immunological un-responsive period difficult to diagnose the disease.

Examples of a diagnostic method to detect such irregular excretion of the bacteria includes isolating and identifying *Mycobacterium avium* subsp. *Paratuberculosis* excreted in feces.

However, the method requires several months to culture *Mycobacterium avium* subsp. *paratuberculosis* in order to recognize the bacterial colonies. Therefore, it is difficult to diagnose the infection at an early stage, and there is a problem in that the infection is spread owing to excretion of the bacteria from a carrier animal during culture. Meanwhile, excretion of the bacteria occurs irregularly and nonpersistently, so there is also a problem in that some infected individuals are not accurately diagnosed.

It takes a long time to culture *Mycobacterium avium* subsp. *paratuberculosis* because *Mycobacterium avium* subsp. *paratuberculosis* belongs to the group III atypical acid-fast bacteria, which are bacteria that have special nutritional requirement and usually proliferate only in a medium supplemented with mycobactin. The bacteria grow very slowly and require 7 to 11 weeks to form visible colonies.

In recent years, there has been suggested a method that enables early diagnosis of presence or absence of *Mycobacterium avium* subsp. *paratuberculosis* in feces by detecting a specific insertion sequence IS900 in DNA of *Mycobacterium avium* subsp. *paratuberculosis* by a polymerase chain reaction (PCR).

However, due to nonpersistent excretion of bacteria, an assured diagnosis was not completed because some individuals cannot be diagnosed or there may be "transited bacteria" which are excreted in feces without chance to invasion into intestinal tissue after oral intake of environmental bacteria in a contaminated farm. Therefore, there has been required an immunological diagnostic method to show evidence that a host is "really infected" with *Mycobacterium avium* subsp. *paratuberculosis*.

As described above, *paratuberculosis* has a long period during which diagnosis is difficult, and all of conventionally prevalent methods of diagnosing *paratuberculosis* are lacking of assurance because the infection time or the like are limited due to its immunological properties. Therefore, there are still many *paratuberculosis*-infected animals, in particular, carrier animals, and the disease spread worldwide, which makes it difficult to eradicate *paratuberculosis*.

Therefore, from the standpoint of animal hygiene, public hygiene, and livestock farming, there is an urgent need to realize prevention of paratuberculosis and eradication in the early stage of infection, and, in particular, there has been desired a diagnostic technique that enables diagnose of an infected animal in the immunological un-responsive stage difficult to diagnose the disease.

On the other hand, together with such direct economical damage due to paratuberculosis, it has recently been in the news that *Mycobacterium avium* subsp. *paratuberculosis* may be involved inhuman Crohn's disease (intractable disease designated by the Ministry of Health and Welfare of Japan) (Collins M T, *Mycobacterium paratuberculosis*: a potential food-borne pathogen? J Dairy Sci 80: 3445-8 (1997); Engstrand L, *Mycobacterium paratuberculosis* and Crohn's disease. Scand J Infect Dis Suppl 98: 27-9, 1995, and Momotani Eiichi "Relationship between Johne's disease and human Crohn's disease-Review-" Journal of Clinical Veterinary Medicine, vol. 19 (No. 7 (additional volume)), 2001).

Therefore, to clarify the relationship between *paratuberculosis* and human Crohn's disease, there has been required a diagnostic technique that enables diagnosis of infection of *Mycobacterium avium* subsp. *paratuberculosis* to human.

The present invention is intended to provide a diagnostic method for paratuberculosis by which an animal infected with *Mycobacterium avium* subsp. *paratuberculosis* can be sensitively diagnosed in the incubation period before the increase of specific antibody level and a large number of specimens can be treated.

DISCLOSURE OF THE INVENTION

The inventors of the present invention have made extensive studies to solve the above-described problems, and in the processes, they have noticed the relationship between interleukin 10 (IL-10), which is one of cytokines and is secreted from animal T-lymphocyte, B-lymphocyte, monocyte/macrophage, or the like and the IFNγ productivity.

When the peripheral blood of an infected cattle with *Mycobacterium avium* subsp. *paratuberculosis* is stimulated in vitro using a *Mycobacterium avium* subsp. *Paratuberculosis* antigen (*Mycobacterium avium* subsp. *paratuberculosis* PPD), IL-10 is produced together with IFNγ, so that it was reported that there is a correlation between the amounts of produced IL-10 and IFNγ. (see Jungersen G, Huda A, Grell S N, Howard C J, 2002. *M. paratuberculosis* specific production of IL-10 after whole blood stimulation is correlated with specific IFN-gamma production and non-stimulated IL-10 levels. 7th International Colloquium on *Paratuberculosis*: Bilbao, Spain: 11-14 Jun. 2002.)

It is generally known that IL-10 has a property to suppress productions of many cytokines. The inventors of the present invention have found out that a decreasing or eliminating phenomenon of a cell-mediated immune response in an animal infected with *Mycobacterium avium* subsp. *Paratuberculosis* induces persistent production of IL-10, to thereby suppress the productivity of IFNγ, resulting in lowering of sensitivity (turning negative) in a cell-mediated immunological diagnostic method.

Then, they have confirmed that, in the case of an infected animal, in vitro stimulation with a *Mycobacterium avium* subsp. *paratuberculosis* antigen to the blood of a subject animal and artificial suppression of a biological activity of IL-10 significantly enhance the amount of produced IFNγ and induce persistent production, so that the infected animal can be distinguished from an non-infected animal by measuring the amounts of produced IFNγ. In particular, they have also confirmed that, even if the subject animal is an infected animal in the immunological un-responsive stage difficult to diagnose the disease, when detection was conventionally impossible by cell-mediated immunological reaction, the cell-mediated immune responses can be enhanced.

Meanwhile, they have found out that the method enables highly sensitive diagnosis of not only *paratuberculosis* but also other diseases caused by *Mycobacteria*, such as tuberculosis and leprosy.

The present invention has been made based on those findings.

That is, according to a first aspect of the present invention, there is provided a diagnostic method for paratuberculosis, characterized by: collecting the blood of a subject animal; adding an anti-interleukin 10 (IL-10) antibody and a *Mycobacterium avium* subsp. *paratuberculosis* antigen to the collected blood followed by culture; and then measuring the amount of produced interferon-γ (IFNγ) in the blood after the culture.

According to a second aspect of the present invention, there is provided a diagnostic method for *paratuberculosis* according to the first aspect of the present invention, characterized in that the amount of produced IFNγ in the blood is measured by an IFNγ ELISA method.

According to a third aspect of the present invention, there is provided a diagnostic method for a mycobacterial disease characterized by: collecting the blood of a subject animal; adding an anti-interleukin 10 (IL-10) antibody and a mycobacterial antigen to the collected blood followed by culture; and then measuring the amount of produced interferon-γ (IFNγ) in the blood after the culture.

BEST MODE FOR CARRYING OUT THE INVENTION

A diagnostic method according to the first aspect of the present invention is characterized by: collecting the blood of a subject animal; adding an anti-interleukin 10 (IL-10) antibody and a *Mycobacterium avium* subsp. *paratuberculosis* antigen to the collected blood followed by culture; and then measuring the amount of produced interferon γ (IFNγ) in the blood after culture.

In the diagnostic method according to the first aspect of the present invention, first, the blood of a subject animal is collected.

The term "subject animal" means an animal that may be infected with *Mycobacterium avium* subsp. *paratuberculosis* and is subjected to a diagnostic method of the present invention. Examples of the animal include ruminants such as cattle (in which contamination of paratuberculosis is spreading in Japan), sheep, goats, and buffalos. Moreover, examples thereof include animals other than the ruminants such as wild deer and animals related to cattle (artiodactyls), which have been reported to be infected with paratuberculosis. Furthermore, in the case where the method is intended for human as a targeted subject animal, it can also be revealed that a *Mycobacterium avium* subsp. *paratuberculosis* antigen is involved in human Crohn's disease (intractable disease designated by Ministry of Health, Labour and Welfare).

To collect blood, an instrument such as a heparin-added vacuum blood collecting tube (Venoject. II, Terumo, Tokyo, Japan) may be used. The site for collection may be the jugular vein of a subject animal.

Note that the collected blood may be diluted and then provided for the following culture, and the dilution concentration is preferably in the range enough for a statistically significant difference to be observed between the case where a subject animal is a healthy animal and the case where it is an infected animal at a time of measuring the yield of IFNγ as described below. For example, the dilution concentration can be 10-fold dilution as those in Examples or can be about 2-fold dilution to enhance the amount of produced IFNγ.

In the diagnostic method according to the first aspect of the present invention, next, an anti-interleukin 10 (IL-10) antibody and a *Mycobacterium avium* subsp. *paratuberculosis* antigen are added to the collected blood followed by culture.

In the case of diagnosing a cattle, any antibody may be used as the anti-IL-10 antibody as long as it has a neutralizing activity to bovine IL-10. For example, CC320 made by Dr. C. J. Howard (Institute of Animal health, Compton, UK) can be used. Note that in the case of performing the present method for animal species other than cattle, there may be used an antibody having a neutralizing activity to IL-10 of each animal species.

The concentration of the anti-IL-10 antibody to be added is preferably in the range enough for a statistically significant difference to be observed between the case where a subject animal is a healthy animal and the case where it is an infected animal at a time of measuring the amount of produced IFNγ as described below. The titer (neutralizing antibody titer) of the antibody to be used varies depending on the production conditions thereof, so that the concentration of the anti-IL-10 antibody to be added cannot be specified exactly. For example, the lower limit of the addition concentration to a medium is preferably higher than 6,400-fold dilution in the case of diluting blood 10-fold followed by culture for 24 to 72 hours, while the upper limit thereof may be appropriately determined in economic terms or so as to prevent adverse effects on a culture medium and is preferably lower than 1,600-fold dilution.

For the *Mycobacterium avium* subsp. *paratuberculosis* antigen, there may be used *Mycobacterium avium* subsp. *Paratuberculosis* PPD (supernatant of a culture of *Mycobacterium avium* subsp. *Paratuberculosis*: johnin PPD), live *Mycobacterium avium* subsp. *Paratuberculosis*, soluble antigen obtained by heat-killed *Mycobacterium avium* subsp. *Paratuberculosis*, or the like. Of those, easily available *Mycobacterium avium* subsp. *paratuberculosis* PPD (johnin) is preferably used because it is normally used in interferon-induced stimulus.

*Mycobacterium avium* subsp. *paratuberculosis* PPD may be prepared in accordance with a method described in, for example, Manual of Standards for Diagnostic Protocols (Office International des Epizooties (OIE) 2000. Manual of standards for diagnostic tests and vaccines. *Paratuberculosis* (Johne's disease).

That is, after culturing *Mycobacterium avium* subsp. *paratuberculosis* (for example, KAG-1) in a Middlebrook 7H9 liquid medium or the like, the bacterial cells are removed from the resultant bacterial culture supernatant, and the resultant culture solution is concentrated by ultrafiltration. To the concentrated solution is added an aqueous solution of 40 w/v % trichloroacetic acid, and the mixture is sufficiently mixed. Then, the resultant precipitates are collected by centrifugation and washed. The washed precipitates are dissolved in a phosphate buffer, and trichloroacetic acid is removed by dialysis. Thereafter, the solution was sterilized by filtration, and the resultant product is used as *Mycobacterium avium* subsp. *paratuberculosis* PPD.

Note that, in the case where the product is not used immediately, it is cryopreserved at −10 to −30° C.

The live *Mycobacterium avium* subsp. *paratuberculosis* and soluble antigen obtained by heat-killed *Mycobacterium avium* subsp. *paratuberculosis* may be prepared in accordance with a method described in Joram J. Buzal, Yasuyuki Mori, Abusaleh M. Bari, Hirokazu Hikono, Aodon-geril, Sachiyo Hirayama, Yujing Shu and Eiichi Momotani (2003). *Mycobacterium avium* subsp. *paratuberculosis* Infection Causes Suppression of RANTES, MCP-1 and TNF-α Expression in Peripheral Blood of Experimentally Infected Cattle. (Infection and Immunity).

That is, the live *Mycobacterium avium* subsp. *paratuberculosis* to be used may be obtained by: culturing *Mycobacterium avium* subsp. *paratuberculosis* (ATCC 10698 strain) at 37° C. for 15 days in a Middlebrook 7H9 broth (Difco Laboratories, USA) supplemented with a Middlebrook OACD Enrichment and mycobactin; collecting the bacterial cells by centrifugation; washing them with a phosphate buffer; suspending them in a phosphate buffer supplemented with 0.01% Tween 80; and adjusting the concentration of the cells to an appropriate level.

On the other hand, the soluble antigen obtained by heat-killed *Mycobacterium avium* subsp. *paratuberculosis* to be used may be obtained by: sterilizing bacterial cells prepared in the same way as that of the above-described live *Mycobacterium avium* subsp. *paratuberculosis* at 121° C. for 15 minutes using an autoclave; placing the bacterial cells and fine beads (mixture of zirconium and silica each having a diameter of 0.5 mm) in a sealed tube; vibrating the tube at a high speed (5,000 times/min) to break the bacterial cells (bead-beader method); centrifuging the resultant at 4° C. and 14,000 (×g); collecting the supernatant; and passing it through a 0.45 μm-filter for sterilization.

Note that, in the case where the product is not used immediately, it is cryopreserved at −50° C. or lower.

With regard to the addition amount of the *Mycobacterium avium* subsp. *paratuberculosis* antigen, the antigen is preferably added in the range enough for a statistically significant difference to be observed between the case where a subject animal is a healthy animal and the case where it is an infected animal at a time of measuring the amount of produced IFNγ as described below. For example, in the case of using *Mycobacterium avium* subsp. *paratuberculosis* PPD as the *Mycobacterium avium* subsp. *paratuberculosis* antigen, a specific addition amount is preferably 0.1 to 1.0 μg/ml, particularly preferably 0.3 to 0.7 μg/ml with respect to a medium.

The culture conditions are not particularly limited as long as an anti-interleukin 10 (IL-10) antibody and a *Mycobacterium avium* subsp. *paratuberculosis* antigen are added to the collected blood followed by culture.

A medium to be used may be appropriately selected from basal media for animal cells such as: an RPMI 1640 medium supplemented with penicillin, streptomycin, and 10% FCS; a Dulbecco's Modified Eagle's Medium; a Ham's Nutrient Mixture F12; and an Eagle's Minimum Essential Medium (EMEM). Of those, preferable is an RPMI 1640 medium supplemented with penicillin, streptomycin, and 10% FCS.

The incubation period may be appropriately determined, corresponding to the medium used, in the range enough for a statistically significant difference to be observed between the case where a subject animal is a healthy animal and the case where it is an infected animal at a time of measuring the amount of IFNγ as described below. For example, in the case of culture using an RPMI 1640 medium supplemented with penicillin, streptomycin, and 10% FCS at 37° C. in a 5% carbon dioxide gas ($CO_2$), the incubation period is normally 24 to 48 hours, while in the case of culture for an animal having lower reactivity, the incubation period may be changed to a longer period of time (for example, 72 hours).

Note that, if necessary, the blood is centrifuged after the culture, and the resultant supernatant may be provided for the following measurement of the amount of produced IFNγ.

In the diagnostic method according to the first aspect of the present invention, next, the amount of produced interferon γ (IFNγ) in the blood after culture is measured.

To measure the amount of produced IFNγ, there may be applied an immunological method that is generally used as a measurement method for cytokines including IFNγ or the like, such as the IFNγ ELISA and a card or test-paper type detection system. Of those, as described in the second aspect, the measurement is preferably performed by the IFNγ ELISA.

The IFNγ ELISA has high sensitivity and good reproducibility and enables examination and measurement of a large number of specimens using a semiautomated machine, so that the method is most often used.

The following are an example of a procedure for the IFNγ ELISA in the case where a subject animal is a cattle.

First, a 96-well ELISA plate coated (immobilized) with anti-bovine IFNγ is prepared. That is, 1) since the concentration (addition amount) of the anti-bovine IFNγ for coating varies depending on the titer of the anti-bovine IFNγ, a preliminary test is firstly performed to determine the concentration (addition amount) so that the antibody is present in a 0.1 M carbon dioxide buffer (pH 9.6) at approximately 1 μg/ml. 2) the determined concentration (addition amount) of the anti-bovine IFNγ is inoculated to adsorb it onto the plate at 4° C. overnight or at 37° C. for 2 hours. 3) Thereafter, the plate is washed twice with PBS supplemented with 0.02% Tween 20.

Subsequently, 100 μl of the supernatant of blood after culture as described above is added to each well of the ELISA plate, followed by sensitization at room temperature for 1 hour. After completion of the sensitization, the plate is washed with PBS supplemented with 0.02% Tween 20. Next, 100 μl of peroxidase-labeled anti-bovine IFNγ that has been diluted 1/50 is added to each well, followed by sensitization at room temperature for 1 hour. Then, the plate is washed with PBS supplemented with 0.02% Tween 20. Moreover, 100 μl of a calorimetric substrate reagent (including tetramethylbenzidine and hydrogen peroxide solution) is added, and the mixture is stirred, followed by a color reaction at room temperature for 10 minutes. The results of the color reaction are read by a microplate reader (such as MTP-120, manufactured by Corona Electric Co., Ltd.), and the IFNγ concentration in each sample is calculated from a curve for known concentrations of serially diluted IFNγ by software (such as Corona MTP-SF5 or Deltadoft).

Note that, in the case where a subject animal is a cattle, use of a kit such as a bovine gamma interferon ELISA kit (BioX S.P.R.L., Marche-en-Famenne, Belgium) enables saving the troubles of preparation of reagents or provision of equipment and may be easily performed in accordance with the manufacturer's instructions, so that the kit is preferable in terms of the reproducibility and a treatment of a large number of specimens.

Note that, in the diagnostic method according to the first aspect of the present invention, the amount of specifically produced IFNγ in the blood is raised by adding an anti-interleukin 10 (IL-10) antibody and a *Mycobacterium avium* subsp. *paratuberculosis* antigen to the blood collected as described above followed by culture, so that there may also be utilized immunological methods having low sensitivity other than the IFNγ ELISA method.

Meanwhile, to measure the amount of produced IFNγ, there can also be applied a method which involves comparing the expression levels of IFNγ by detecting the mRNA of IFNγ in peripheral blood cells, not IFNγ as a protein, through an RT-PCR method or a real-time RT-PCR method. However, the method requires RNA extraction, reagents for PCR reactions, and equipment such as a thermal cycler unlike an immunological detection method such as the IFNγ ELISA method, so that the immunological detection method such as the IFNγ ELISA method is the easiest in terms of a treatment of a large number of specimens.

The diagnostic method according to the first aspect of the present invention is described above, and it may also be applied not only to *Mycobacterium avium* subsp. *paratuberculosis* but also to mycobacterial disease caused by a Mycobacteria. The present invention according to the third aspect of the present invention provides a diagnostic method for such Mycobacteria.

That is, the diagnostic method according to the third aspect of the present invention is a diagnostic method for a mycobacterial disease characterized by comprising: collecting the blood of a subject animal; adding an anti-interleukin 10 (IL-10) antibody and a mycobacterial antigen to the collected blood followed by culture; and then measuring the amount of interferon γ (IFNγ) in the blood after culture.

Examples of the mycobacterial disease include diseases caused by acid-fast bacteria, such as tuberculosis and leprosy. In the case where the mycobacterial disease is tuberculosis, examples of a subject animal include human, cattle, and other animals that may be infected with tuberculosis, and examples of the mycobacterial antigen include a tuberculosis antigen (for example, tuberculin PPD). Meanwhile, in the case where the mycobacterial disease is leprosy, examples of a subject animal include human and other animals that may be infected with leprosy, and examples of the mycobacterial antigen include a leprosy antigen (for example, lepromin).

Hereinafter, the present invention will be described in more detail by way of Examples.

Experiment 1

Relationship Between Addition Concentration of Anti-IL-10 Antibody and IFNγ Productivity A comparison was performed with regard to the aggravation degrees of the IFNγ productivities enhanced by johnin PPD in culture of peripheral bloods of cattle infected with *Mycobacterium avium* subsp. *paratuberculosis* and non-infected control cattle each added with an anti-IL-10 antibody.

(1) About Cattle Infected with *Mycobacterium avium* subsp. *paratuberculosis* and Non-Infected Control Cattle For cattle infected with *Mycobacterium avium* subsp. *paratuberculosis*, 5 Holsteins were used after being subjected to oral administration of $20.7 \times 10^8$ CFU of *Mycobacterium avium* subsp. *paratuberculosis* in the first one week of birth and then castrated (25-months old at the time of experimental blood collection). Those cattle had positive results in the IFNγ ELISA, while they had negative results in clinical signs such as diarrhea and detection of a specific antibody by ELISA as well as in a PCR test for feces.

On the other hand, for non-infected control cattle, there were used 5 castrated cattle (Holsteins) having the same ages as the cattle infected with *Mycobacterium avium* subsp. *paratuberculosis*.

From the jugular vein of each of the cattle infected with *Mycobacterium avium* subsp. *paratuberculosis* and the non-infected control cattle, the peripheral blood was collected by means of a heparin-added vacuum blood collecting tube (Venoject II, Terumo, Tokyo, Japan).

(2) Culture of Peripheral Blood

Before adding an anti-IL-10 antibody and *Mycobacterium avium* subsp. *paratuberculosis* PPD to the collected peripheral blood followed by culture, first, *Mycobacterium avium* subsp. *paratuberculosis* PPD was prepared in accordance with "Manual of Standards for Diagnostic Protocols (Office International des Epizooties (OIE) 2000. Manual of standards for diagnostic tests and vaccines. Paratuberculosis (Johne's disease).

That is, as a strain for production of peripheral blood, there was used a *Mycobacterium avium* subsp. *paratuberculosis* KAG-1 strain that is an isolate of wild-type *Mycobacterium avium* subsp. *paratuberculosis* and the strain has been cloned so as to have an ability to proliferate in a medium for producing a PPD antigen, said medium containing no OACD complex. Note that the KAG-1 strain was cryopreserved at −80° C. until use.

The above-described KAG-1 strain was inoculated to a Middlebrook 7H9 liquid medium supplemented with 2 µg/l mycobactin and cultured at 37° C. for 2 months. Note that a Middlebrook OACD enrichment to be usually supplemented to a Middlebrook 7H9 liquid medium in culturing *Mycobacterium avium* subsp. *paratuberculosis* was not supplemented because of protein-free culture.

After completion of the culture, the resultant bacterial suspension was sterilized at 100° C. for 3 hours, and then the bacterial cells were removed by filtration and centrifugation. The culture solution was concentrated to about one fifth of its original volume by ultrafiltration. To 9 parts by volume of the concentrated solution was added 1 part by volume of an aqueous solution of 40 w/v % trichloroacetic acid, and the whole was sufficiently mixed. The generated precipitates were collected by centrifugation and washed with 4 w/v % trichloroacetic acid. The precipitates were dissolved in a phosphate buffer having a volume of one fifth of the concentrated solution, and trichloroacetic acid was removed by dialysis. Thereafter, the solution was sterilized by filtration, and the resultant product was used as *Mycobacterium avium* subsp. *paratuberculosis* PPD. Note that the product was stored at −20° C. until use.

Each of the collected peripheral bloods was diluted 10-fold with an RPMI 1640 medium supplemented with penicillin, streptomycin, and 10% fetal calf serum (FCS) and added to each well of a 48-well tissue culture plate (Sumitomo Bakelite Co., Ltd., Tokyo). *Mycobacterium avium* subsp. *paratuberculosis* PPD was added thereto so as to have a final concentration of 5 μg/ml, and an anti-IL-10 antibody was further added so as to have a concentration of 1/100 (dilution rate 100-fold), 1/400 (dilution rate 400-fold), 1/1,600 (dilution rate 1,600-fold), 1/6,400 (dilution rate 6,400-fold), 1/25,600 (dilution rate 25,600-fold), 1/102,400 (dilution rate 102,400-fold), or 1/409,600 (dilution rate 409,600-fold) of the original concentration, followed by culture at 37° C. in 5% $CO_2$ for 48 hours.

Meanwhile, to the peripheral blood collected from each cattle infected with *Mycobacterium avium* subsp. *paratuberculosis*, instead of the anti-IL-10 antibody, 50 μg/ml normal mouse IgG having the common isotype was added as a control so as to have the same dilution rate as that of the antibody.

For the anti-IL-10 antibody, there was used CC320 made by Dr. C. J. Howard (Institute of Animal health, Compton, UK).

After completion of the culture, the plate was centrifuged at 1,500 rpm (400 G) for 5 minutes, and each culture supernatant was separated for detection of IFNγ.

(3) Measurement of Amount of Produced IFNγ

The amount of produced IFNγ in each culture supernatant was measured using a bovine gamma interferon ELISA kit (BioX S.P.R.L., Marche-en-Famenne, Belgium) in accordance with the manufacturer's instructions of the kit.

Figure 2:
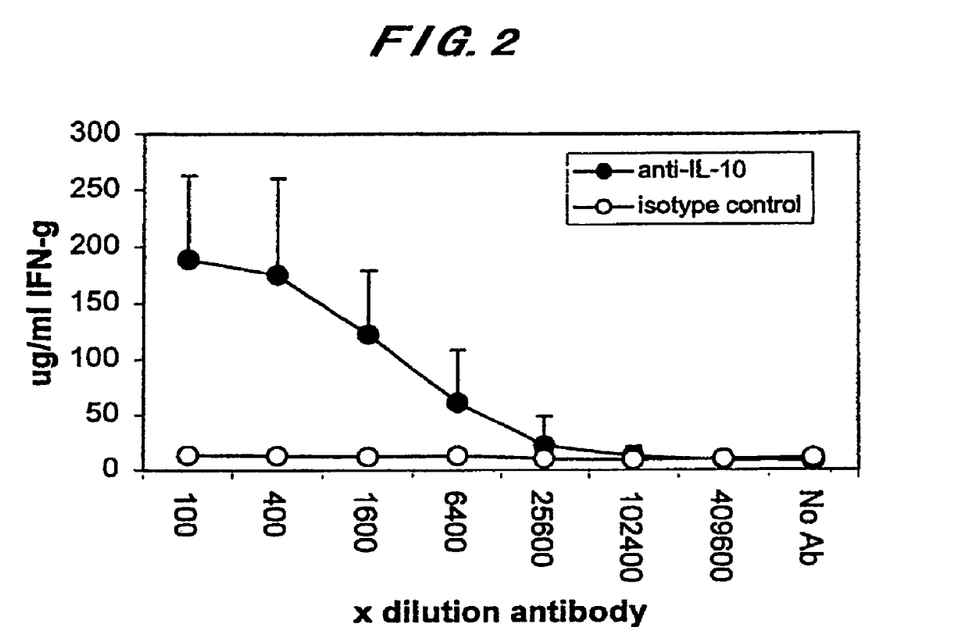
FIG. 2 shows the comparison results between the dependency of the amounts of produced IFNγ in the cattle infected with *Mycobacterium avium* subsp. *Paratuberculosis* on the concentrations of anti-IL-10 antibody and that in the case of adding the mouse IgG having the same isotype as the antibody in Experiment 1.

There were calculated the mean values of the amounts of produced IFNγ in 5 cattle infected with *Mycobacterium avium* subsp. *paratuberculosis* at the respective addition concentrations of the antibody both in the case of adding the anti-IL-10 antibody followed by culture and in the case of adding IgG followed by culture. FIG. 2 shows the comparison results between the dependency of the amounts of produced IFNγ in the cattle infected with *Mycobacterium avium* subsp. *paratuberculosis* on the concentrations of anti-IL-10 antibody and that in the case of adding the mouse IgG having the same isotype as the antibody.

Figure 3:
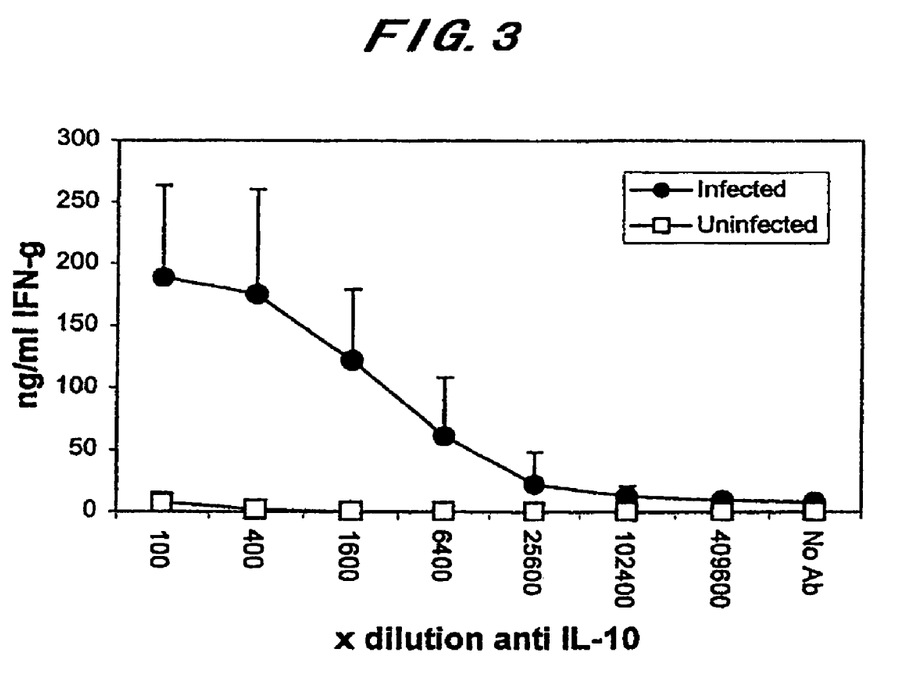
FIG. 3 shows the comparison results between the dependency of the amounts of produced IFNγ in the cattle infected with *Mycobacterium avium* subsp. *paratuberculosis* on the concentrations of anti-IL-10 antibody and that in the case of the (non-infected) control cattle in Experiment 1.

Meanwhile, similarly, there were also calculated the mean values of the amounts of produced IFNγ in 5 non-infected control cattle at the respective addition concentrations of the antibody. FIG. 3 shows the comparison results between the dependency of the amounts of produced IFNγ in the cattle infected with *Mycobacterium avium* subsp. *paratuberculosis* and that in the non-infected control cattle.

In the peripheral blood samples of the cattle infected with *Mycobacterium avium* subsp. *paratuberculosis* to which the anti-IL-10 antibody had been added followed by culture, there was observed, in all the 5 infected cattle, statistically significant increase in the amounts of produced IFNγ produced by stimulation with *Mycobacterium avium* subsp. *paratuberculosis* PPD, which correlate with the addition concentrations of the anti-IL-10 antibody (see FIG. 2).

That is, as is clear from FIG. 2, in the case of adding an anti-bovine IL-10, the mean values of the amounts of produced IFNγ are clearly increased from at about 1/25,600 (dilution rate 25,600-fold), and the amounts of produced IFNγ at 1/400 to 1/100 (dilution rate 400 to 100-fold) reached nearly a plateau value.

On the other hand, in the samples of the peripheral bloods of the cattle infected with *Mycobacterium avium* subsp. *paratuberculosis* to which IgG had been added followed by culture, no changes in the amounts of produced IFNγ due to the addition concentrations of the antibody were induced in all the 5 infected cattle (see FIG. 2).

As is clear from FIG. 2, the results of comparison analysis using analysis of variance (ANOVA) between the amounts of produced IFNγ in the case of adding the anti-IL-10 antibody and those in the case of adding IgG revealed that there are significant differences (P<0.001) calculated by the analysis of variance at antibody dilution rates of 100-fold to 1,600-fold.

Moreover, in the samples of the peripheral blood of the 5 non-infected control cattle, no changes in the amounts of produced IFNγ due to the addition concentrations of the antibody were induced in all the 5 infected cattle (see FIG. 3).

As is clear from FIG. 3, in the case of adding the anti-IL-10 antibody, the results of comparison analysis using the analysis of variance (ANOVA) between the amounts of produced IFNγ in the cattle infected with *Mycobacterium avium* subsp. *paratuberculosis* and those in the non-infected control cattle revealed that there are significant differences (P<0.001) calculated by the analysis of variance at antibody dilution rates of 100-fold to 1,600-fold.

Such dependency of the amounts of produced IFNγ in the peripheral blood of the cattle infected with *Mycobacterium avium* subsp. *paratuberculosis* on the anti-IL-10 antibody concentrations proves that the IFNγ productivity was enhanced by stimulation with the *Mycobacterium avium* subsp. *paratuberculosis* antigen but was significantly suppressed by IL-10 that was concurrently produced by the stimulation with the antigen.

The present experiment revealed that, when an anti-IL-10 antibody is added to the peripheral blood of a subject animal stimulated with a *Mycobacterium avium* subsp. *paratuberculosis* antigen followed by culture, the IFNγ productivity specific to the antigen may be drastically enhanced even in an infected animal having a decreased cell-mediated immune response, resulting in reliable and sensitive diagnosis of an animal infected with *Mycobacterium avium* subsp. *paratuberculosis*.

Experiment 2

In the Case of Incubation Period of 24 Hours

Figure 4:
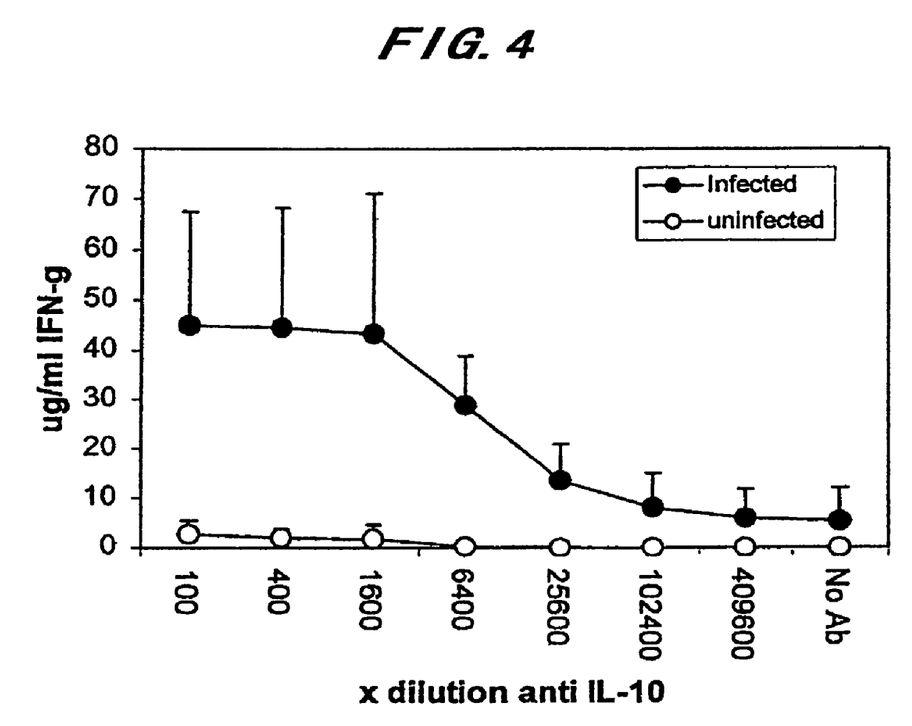
FIG. 4 shows the comparison results between the dependency of the amounts of produced IFNγ in the cattle infected with *Mycobacterium avium* subsp. *Paratuberculosis* on the concentrations of anti-IL-10 antibody and that in the case of the (non-infected) control cattle in Experiment 2.

The same procedures as that in Example 1 were repeated except that the incubation period was shortened to 24 hours, and the mean values at the respective addition concentrations of the antibody were calculated for the amounts of produced IFNγ in the 5 cattle infected with *Mycobacterium avium* subsp. *paratuberculosis* and the amounts of produced IFNγ in the 5 non-infected control cattle, in the case where the anti-IL-10 antibody had been added followed by culture. FIG. 4 shows the comparison results between the dependency of the amounts of produced IFNγ in the cattle infected with *Mycobacterium avium* subsp. *paratuberculosis* on the anti-IL-10 antibody concentrations and that of the non-infected control cattle.

In the peripheral blood samples of the 5 cattle infected with *Mycobacterium avium* subsp. *paratuberculosis* to which the anti-IL-10 antibody had been added followed by culture, the amounts of produced IFNγ produced by stimulation with *Mycobacterium avium* subsp. *paratuberculosis* PPD in all the 5 control cattle was observed to statistically significantly increase correlating with the addition concentration of the added anti-IL-10 antibody (see FIG. 4).

On the other hand, in the peripheral blood samples of all the 5 non-infected control cattle, no changes were induced by addition of any concentration of the antibody (see FIG. 4).

As is clear from FIG. 4, the results of comparison analysis using the analysis of variance (ANOVA) between the amounts of produced IFNγ in the cattle infected with *Mycobacterium avium* subsp. *paratuberculosis* and those in the non-infected control cattle revealed that there are significant differences (P<0.001) calculated by the analysis of variance at antibody dilution rates of 100-fold to 1,600-fold. Meanwhile, in the case of the dilution rate of 6,400-fold, the significant difference was found to be p<0.01.

The present experiment revealed that, when an anti-IL-10 antibody is added to the peripheral blood of a subject animal stimulated with a *Mycobacterium avium* subsp. *paratuberculosis* antigen followed by culture, even if the incubation period is 24 hours, the IFNγ productivity specific to the antigen can be drastically enhanced even in an infected animal having a decreased cell-mediated immune response, resulting in reliable and sensitive diagnosis of an animal infected with *Mycobacterium avium* subsp. *paratuberculosis*.

Meanwhile, it is revealed that, in the case where the culture was performed for 24 hours using CC320 as the anti-IL-10 antibody, more effective results are obtained by adjusting the addition concentration of the antibody to be 1,600-fold or less.

Experiment 3

The Case of Incubation Period of 72 Hours

Figure 5:
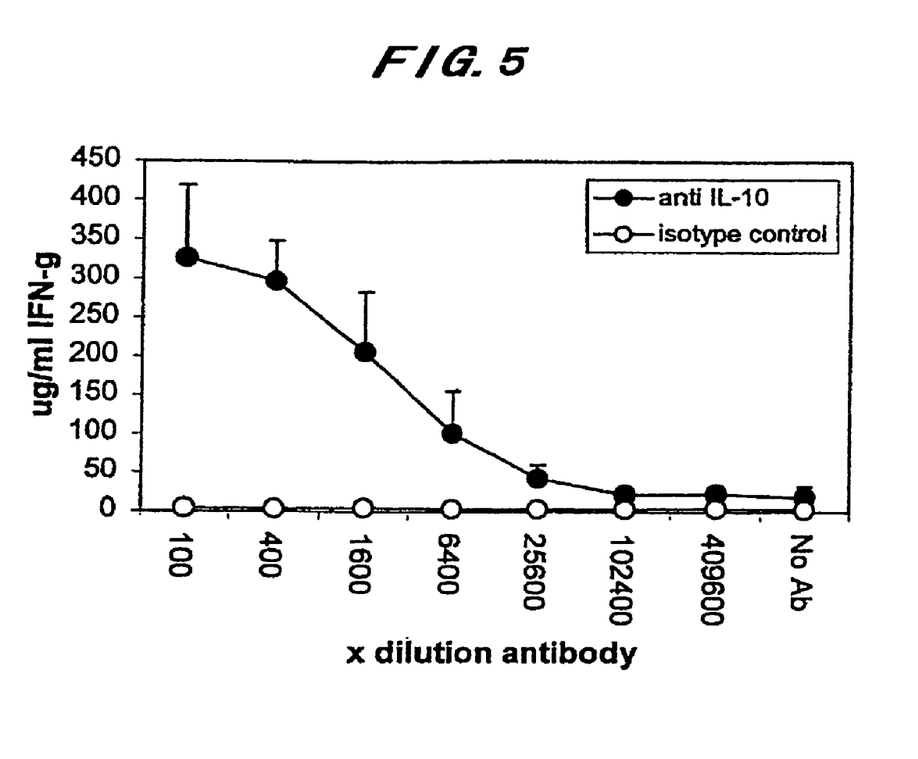
FIG. 5 shows the comparison results between the dependency of the amounts of produced IFNγ in the cattle infected with *Mycobacterium avium* subsp. *Paratuberculosis* on the concentrations of anti-IL-10 antibody and that in the case of adding the mouse IgG having the same isotype as the antibody in Experiment 3.

The same procedures as that in Experiment 1 were repeated except that the incubation period was elongated to 72 hours, and the mean values of the amounts of produced IFNγ in 5 cattle infected with *Mycobacterium avium* subsp. *paratuberculosis* at the respective addition concentrations of the antibody were calculated for the case of adding the anti-IL-10 antibody followed by culture and the case of adding IgG followed by culture. FIG. 5 shows the comparison results between the dependency of the amounts of produced IFNγ in the cattle infected with *Mycobacterium avium* subsp. *paratuberculosis* on the concentrations of anti-IL-10 antibody and that in the case of adding the mouse IgG having the same isotype as the antibody.

In the peripheral blood samples of the cattle infected with *Mycobacterium avium* subsp. *paratuberculosis* to which the anti-IL-10 antibody had been added followed by culture, there was observed statistically significant increase in the amounts of produced IFNγ produced by stimulation with *Mycobacterium avium* subsp. *paratuberculosis* PPD, which correlate with the addition concentrations of the added anti-IL-10 antibody, in all the 5 infected cattle (see FIG. 5). In particular, in the case of adding 1/100 (dilution rate at 100-fold) of the antibody, the mean of the amounts of production was found to be more than 300 μg/ml.

On the other hand, in the samples of the peripheral bloods of the cattle infected with *Mycobacterium avium* subsp. *paratuberculosis* to which IgG had been added followed by culture, no changes in the amounts of produced IFNγ due to the concentration of antibody to be added were induced in all the 5 infected cattle (see FIG. 5).

As is clear from FIG. 5, the results of comparison analysis using the analysis of variance (ANOVA) between the amounts of produced IFNγ in the case of adding the anti-IL-10 antibody and those in the case of adding IgG revealed that there are significant differences (P<0.001) calculated by the analysis of variance at antibody dilution rates of 100-fold to 1,600-fold.

The present experiment revealed that, when an anti-IL-10 antibody is added to the peripheral blood of a subject animal stimulated with a *Mycobacterium avium* subsp. *paratuberculosis* antigen followed by culture, even if the incubation period is 72 hours, the IFNγ productivity specific to the antigen can be drastically enhanced even in an infected animal having a decreased cell-mediated immune response, resulting in reliable and sensitive diagnosis of an animal infected with *Mycobacterium avium* subsp. *paratuberculosis*.

Comparative Experiment 1

The Case of Using Con A

The same procedures as that in Experiment 1 were repeated except that concanavalin A was used instead of *Mycobacterium avium* subsp. *paratuberculosis* PPD, and the mean values at the respective addition concentrations of the antibody were calculated for the amounts of produced IFNγ in the 5 cattle infected with *Mycobacterium avium* subsp. *paratuberculosis* and the amounts of produced IFNγ in the 5 non-infected control cattle, in the case where the anti-IL-10 antibody had been added followed by culture. Note that Con A is one of lectins that may nonspecifically stimulate immunocytes.

Figure 6:
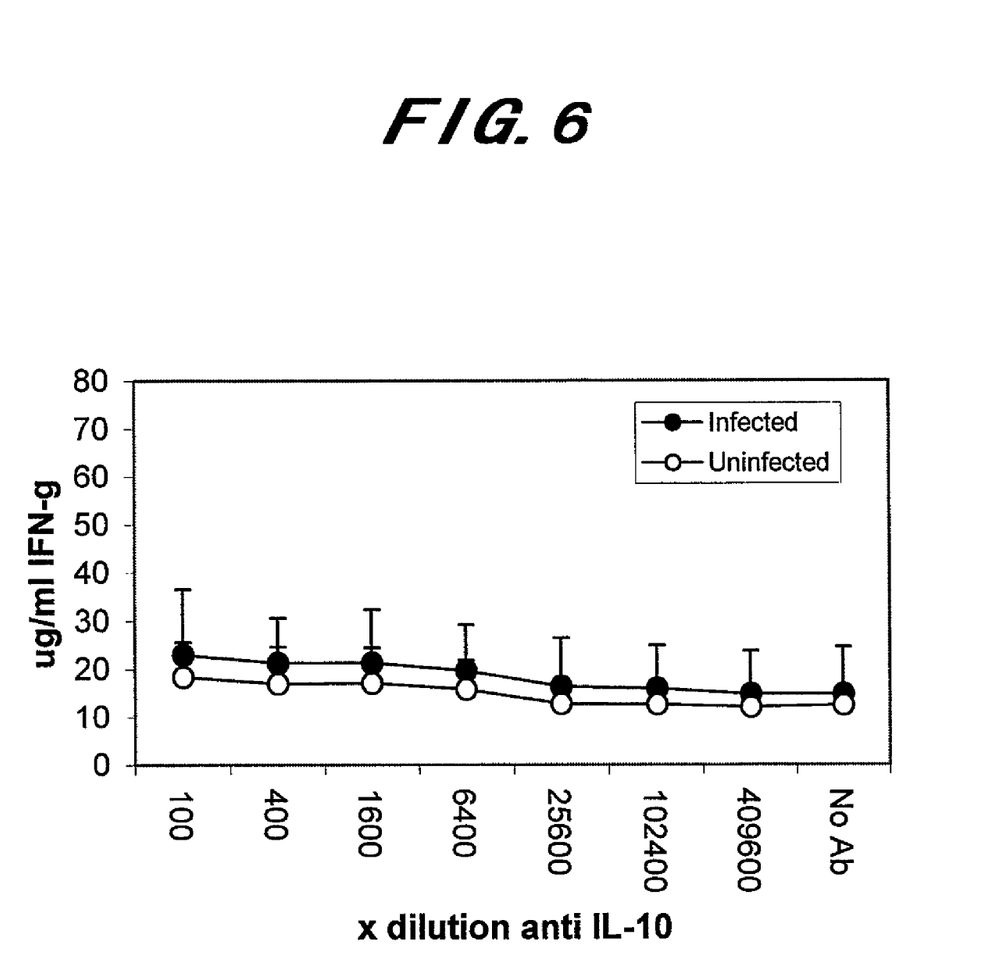
FIG. 6 shows the comparison results between the dependency of the amounts of produced IFNγ in the cattle infected with *Mycobacterium avium* subsp. *Paratuberculosis* on the concentrations of anti-IL-10 antibody and that in the case of the (non-infected) control cattle in Comparative Experiment 1.

FIG. 6 shows the comparison results between the dependency of the amounts of produced IFNγ in the cattle infected with *Mycobacterium avium* subsp. *paratuberculosis* on the anti-IL-10 antibody concentrations and that in the non-infected control cattle.

As a result, although IFNγ was produced both in the cattle infected with *Mycobacterium avium* subsp. *paratuberculosis* and in the non-infected control cattle, no changes in the amounts of produced IFNγ due to the addition concentrations of the added anti-IL-10 antibody were induced (see FIG. 6).

The present comparative experiment revealed that reliable and sensitive diagnosis of animals infected with *Mycobacterium avium* subsp. *paratuberculosis* requires antigen-specific stimulation with a *Mycobacterium avium* subsp. *paratuberculosis* antigen, not nonspecific stimulation, in adding an anti-IL-10 antibody to the peripheral blood of a subject animal followed by culture.

Comparative Experiment 2

The same procedures as that in Experiment 1 were repeated except that *Mycobacterium avium* subsp. *paratuberculosis* PPD was not used, and the mean values at the respective addition concentrations of the antibody were calculated for the amounts of produced IFNγ in the 5 cattle infected with *Mycobacterium avium* subsp. *paratuberculosis* and the amounts of produced IFNγ in the 5 non-infected control cattle, in the case where the anti-IL-10 antibody had been added followed by culture.

Figure 7:
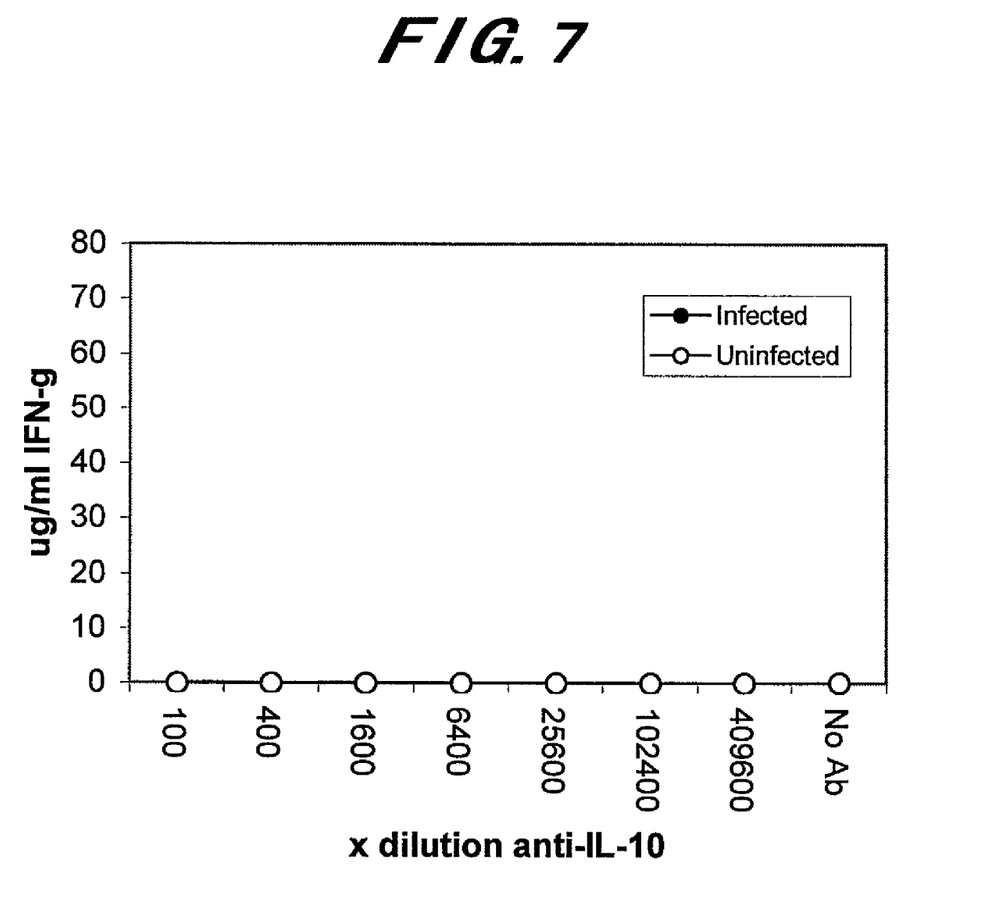
FIG. 7 shows the comparison results between the dependency of the amounts of produced IFNγ in the cattle infected with *Mycobacterium avium* subsp. *Paratuberculosis* on the concentrations of anti-IL-10 antibody and that in the case of the (non-infected) control cattle in Comparative Experiment 2.

FIG. 7 shows the comparison results between the dependency of the amounts of produced IFNγ in the cattle infected with *Mycobacterium avium* subsp. *paratuberculosis* on the anti-IL-10 antibody concentrations and that in the non-infected control cattle.

As a result, in both the cattle infected with *Mycobacterium avium* subsp. *paratuberculosis* and the non-infected control cattle, the amounts of produced IFNγ were not significantly induced at every addition concentration of the anti-IL-10 antibody (see FIG. 7).

The present comparative experiment revealed that reliable and sensitive diagnosis of an animal infected with *Mycobacterium avium* subsp. *paratuberculosis* requires antigen-specific stimulation with a *Mycobacterium avium* subsp. *paratuberculosis* antigen in adding an anti-IL-10 antibody to the peripheral blood of a subject animal followed by culture.

Those experimental results revealed that, as described in the first aspect of the present invention, a method comprising: collecting the blood of a subject animal; adding an anti-interleukin 10 (IL-10) antibody and a *Mycobacterium avium* subsp. *paratuberculosis* antigen to the collected blood followed by culture; and then measuring the amount of produced interferon γ (IFNγ) in the blood after culture enables sensitive diagnosis in the sub-clinical stage of infection before the specific antibody level increases and a treatment of a large number of specimens.

INDUSTRIAL APPLICABILITY

The diagnostic method according to the first aspect of the present invention enables sensitive diagnosis of an animal infected with *Mycobacterium avium* subsp. *paratuberculosis* in the sub-clinical stage of infection before the specific antibody level increases and a treatment of a large number of specimens.

Therefore, the diagnostic method according to the first aspect of the present invention is intended to eliminate animals infected with *Mycobacterium avium* subsp. *paratuberculosis* to establish a clean animal group that is not infected with *Mycobacterium avium* subsp. *paratuberculosis* and to provide an aggressive breakthrough for measures to fight against *paratuberculosis* that may inflict a worldwide economical loss, cause Crohn's disease, or the like.

Meanwhile, the diagnostic method according to the third aspect of the present invention enables reliable and sensitive diagnosis of animals infected with mycobacterial disease such as tuberculosis or leprosy regardless of the course of infection and treatment of a large number of specimens.

The invention claimed is:

1. A cell-mediated immunological diagnostic method for paratuberculosis characterized by comprising:

collecting blood of a subject animal, thereby providing collected blood;

adding (a) an anti-interleukin 10 (IL-10) antibody and (b) a stimulus which induces cell-mediated immunological reaction against *Mycobacterium avium* subsp. *paratuberculosis* in the collected blood, to the collected blood, so as to induce said cell-mediated immunological reaction, wherein said stimulus added to the collected blood is a *Mycobacterium avium* subsp. *paratuberculosis* antigen;

subsequent to said adding, measuring an amount of produced interferon-γ (IFNγ) in the blood;

subsequent to said measuring, comparing between amounts of the produced interferon-γ (IFNγ) measured in the subject animal and that in a non-infected control animal; and distinguishing the subject animal from a non-infected control animal in a case where a statistically significant increase in amounts of produced interferon-γ (IFNγ) is measured in the subject animal.

2. A cell-mediated immunological diagnostic method for paratuberculosis according to claim 1, characterized in that the amount of produced IFNγ in the blood is measured by an IFNγ ELISA method.

3. A cell-mediated immunological diagnostic method according to claim 1, characterized in that said stimulus added to the collected blood is selected from the group consisting of (i) *Mycobacterium avium* subsp. *paratuberculosis* PPD, (ii) live *Mycobacterium avium* subsp. *paratuberculosis* and (iii) soluble antigen obtained by sterilizing *Mycobacterium avium* subsp. *paratuberculosis* with heat to break the bacterial cells and collecting the supernatant.

4. A cell-mediated immunological diagnostic method for paratuberculosis according to claim 1, wherein culturing is performed between said adding and said measuring.

* * * * *